United States Patent [19]

Kreisher et al.

[11] Patent Number: 4,576,693

[45] Date of Patent: Mar. 18, 1986

[54] NUCLEIC ACID SEQUENCING ELECTROPHORESIS APPARATUS AND METHOD OF FABRICATING

[75] Inventors: John H. Kreisher, Ridgefield; Charles A. Nalbantian, New Haven, both of Conn.

[73] Assignee: International Biotechnologies, Inc., New Haven, Conn.

[21] Appl. No.: 691,057

[22] Filed: Jan. 14, 1985

[51] Int. Cl.⁴ ............................................. G01N 27/26
[52] U.S. Cl. .............................. 204/180.1; 204/299 R; 249/160; 249/167; 264/219; 264/261; 264/313
[58] Field of Search .................. 249/82, 160, 167; 264/219, 313, 216, 337, 2.2, 261; 204/180 G, 299 R; 425/451.9

[56] References Cited

U.S. PATENT DOCUMENTS

| | | | |
|---|---|---|---|
| 3,129,158 | 4/1964 | Raymond et al. | 204/180 G |
| 4,142,960 | 3/1979 | Hahn et al. | 204/299 R |
| 4,151,065 | 4/1979 | Kaplan | 204/180 G |
| 4,234,400 | 11/1980 | Kaplan | 204/180 G |

*Primary Examiner*—Jan Silbaugh
*Assistant Examiner*—MaryLynn Fertig
*Attorney, Agent, or Firm*—Bachman & LaPointe

[57] ABSTRACT

An electrophoresis apparatus including a mold for forming a vertically disposed electrophoresis gel slab where the slab is of uniformly increasing thickness from top to bottom and method of fabricating the mold and the gel slab.

19 Claims, 10 Drawing Figures

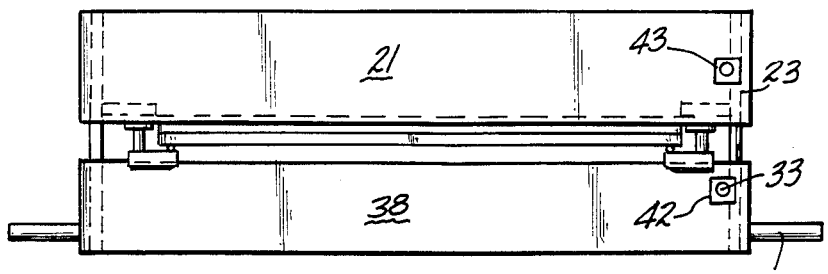
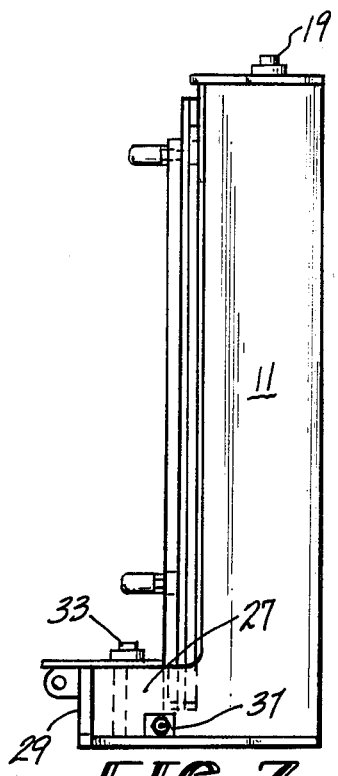
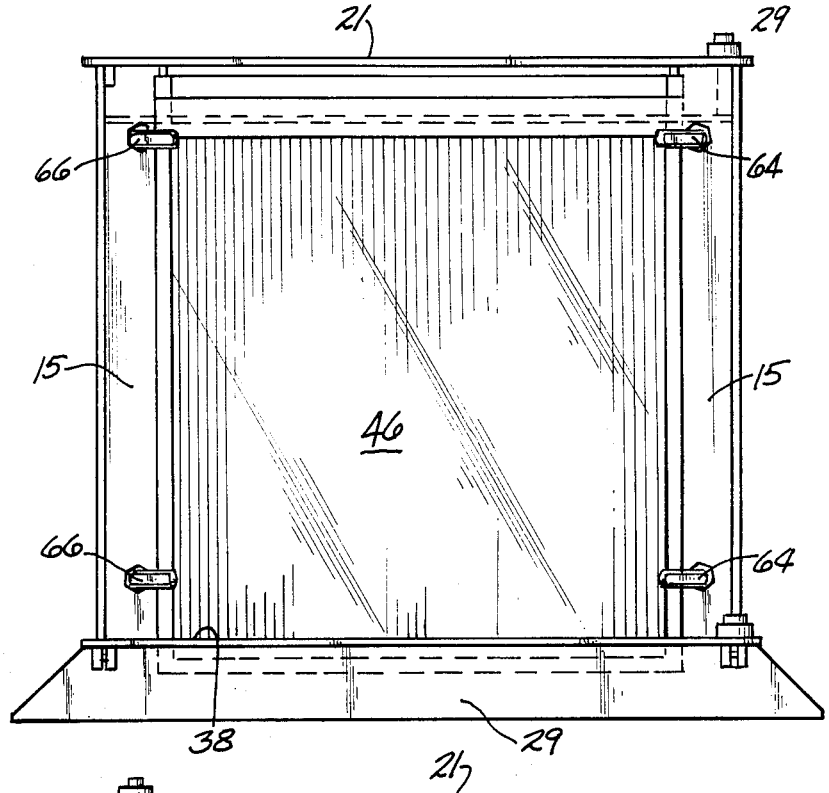
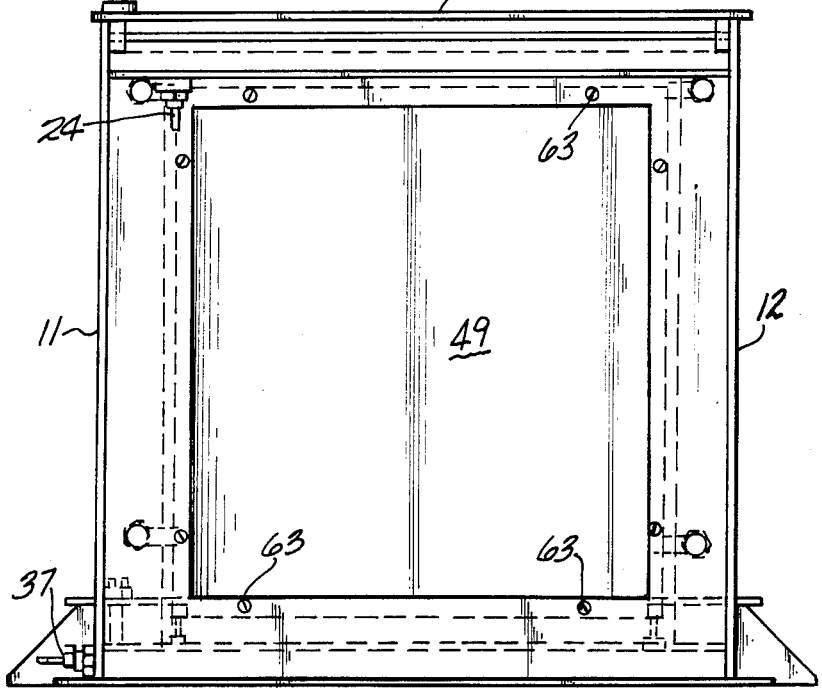

NUCLEIC ACID SEQUENCING ELECTROPHORESIS APPARATUS AND METHOD OF FABRICATING

BACKGROUND OF THE INVENTION

The present invention relates to electrophoresis and relates in particular to a gel mold apparatus, a method of fabricating the mold apparatus and a method of molding a wedge shaped electrophoresis gel slab.

Many gel slabs are molded horizontally as shown and described in U.S. Pat. Nos. 4,151,065 and 4,234,400, both entitled HORIZONTAL SLAB GEL ELECTROPHORESIS and both issued to Kaplan et al. on Apr. 24, 1979 Nov. 18, 1980, respectively.

While horizontal gel slab arrangements are operative, it is desirable to mold slabs vertically for optimum results.

In particular, it is desirable to mold gels vertically with increasing thickness of gel slab from top to bottom simulating an inverted wedge or inverted V-shape configuration in cross-section.

Since vertical gel slabs are molded between flat glass mold plates with a peripheral gasket or spacer sandwiched between the plates, difficulty has been encountered in developing a mold which produces a relatively thin gel slab having a greater thickness at the bottom than the thickness at the top.

One prior art technique has been to use the customary flat glass mold plates with a thin tapered spacer.

Since the spacers are of the order of 0.2 to 1.0 millimeter in thickness and the taper can be as slight as 0.014 millimeters per running centimeter, one can see that it is very difficult to prepare such spacers accurately.

SUMMARY OF THE INVENTION

Consequently, it is a principal feature of the present invention to provide a novel vertical electrophoresis gel mold apparatus.

It is a further feature of the invention to provide a novel method of fabricating the mold.

A still further feature of the invention is the provision of a method of molding a relatively thin gel slab vertically where the slab is of increasing thickness from top to bottom so that its cross-sectional configuration is shaped like an inverted wedge or an inverted V.

A further feature of the invention is the provision of a mold apparatus where the spacer is of uniform thickness and need not be tapered.

The invention also provides a novel arrangement of buffer reservoirs with convenient, quick operating bottom drains and stopcocks or petcocks.

A further feature of the invention is the provision of shield units for insulating, optimizing and equalizing heat throughout the gel.

The invention also contemplates convenient quick operating latch mechanisms settable in at least two positions for retaining the shields and for applying the appropriate clamping pressure to the mold plates.

A mold apparatus embracing certain principles of the present invention may comprise a pair of plates each having a first flat surface, said plates being spaced apart by a ribbon of gasket material of uniform thickness, spaced margins of one of said plates being offset from said flat surface to define second surfaces, said second surfaces being inclined relative to said first surface and means for clamping the plates together with the gasket material sandwiched between said surfaces.

A method of fabricating the mold apparatus may comprise the steps of providing two mold plates each having generally flat primary surfaces, establishing a pair of matching, inclined secondary surfaces on opposed margins of one of said plates, said secondary surfaces being offset from the adjacent primary surface, disposing a ribbon of gasket material of uniform thickness in areal contact with both said secondary surfaces, and clamping the plates together with the gasket material sandwiched between the plates.

A method of creating a vertical gel slab having an inverted wedge shape where the thickness of the slab at the top is of the order of 0.2 mm to 0.4 mm and the bottom thickness is of the order of 0.8 mm to 1.0 mm may comprise the steps of forming the mold as related above and pouring a suitable gel into the open top of the mold.

BRIEF DESCRIPTION OF THE DRAWINGS

Other features and advantages of the invention will become more apparent from an examination of the succeeding specification when read in conjunction with the appended drawings, in which:

FIG. 5 is a front elevation of the apparatus of FIG. 1;

FIG. 6 is a top view of FIG. 5;

FIG. 7 is an elevation of the right side of FIG. 5; and

FIG. 8 is a real elevation of the illustration of FIG. 5.

DESCRIPTION OF THE PREFERRED EMBODIMENT

Figure 1:
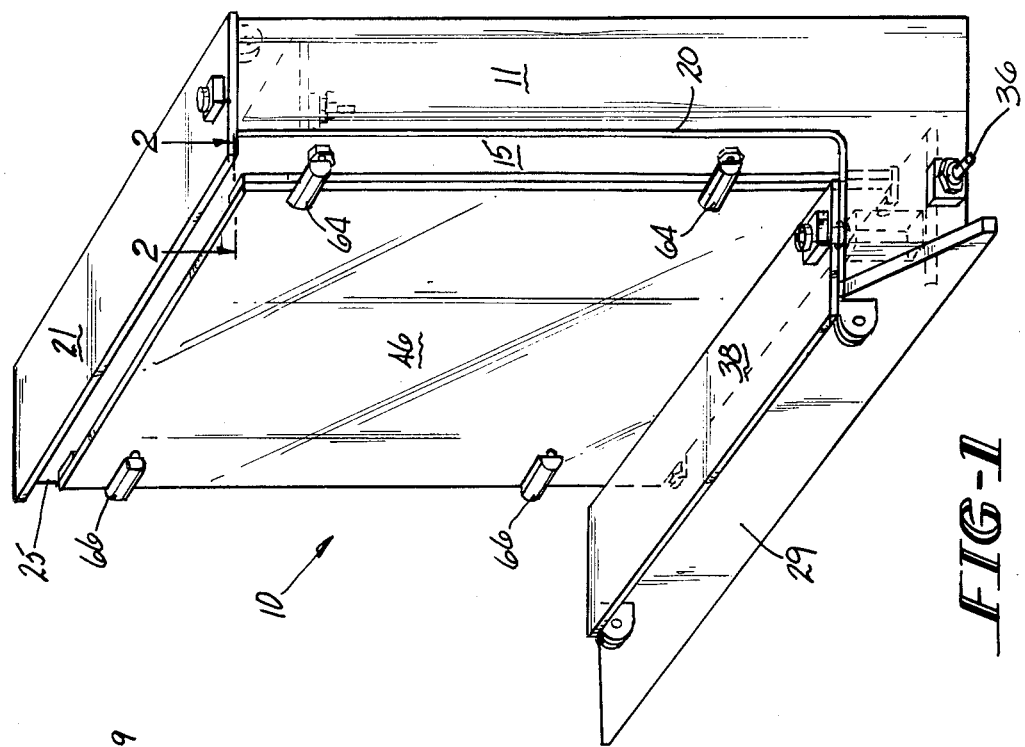
FIG. 1 is a perspective view of the assembled apparatus.
Figure 2:
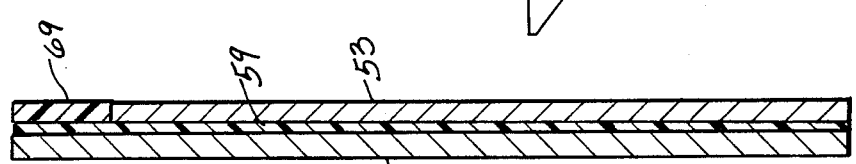
FIG. 2 is a vertical section of the mold plates in the region of the spacer as viewed in the plane represented by the line 2—2.
Figure 3:
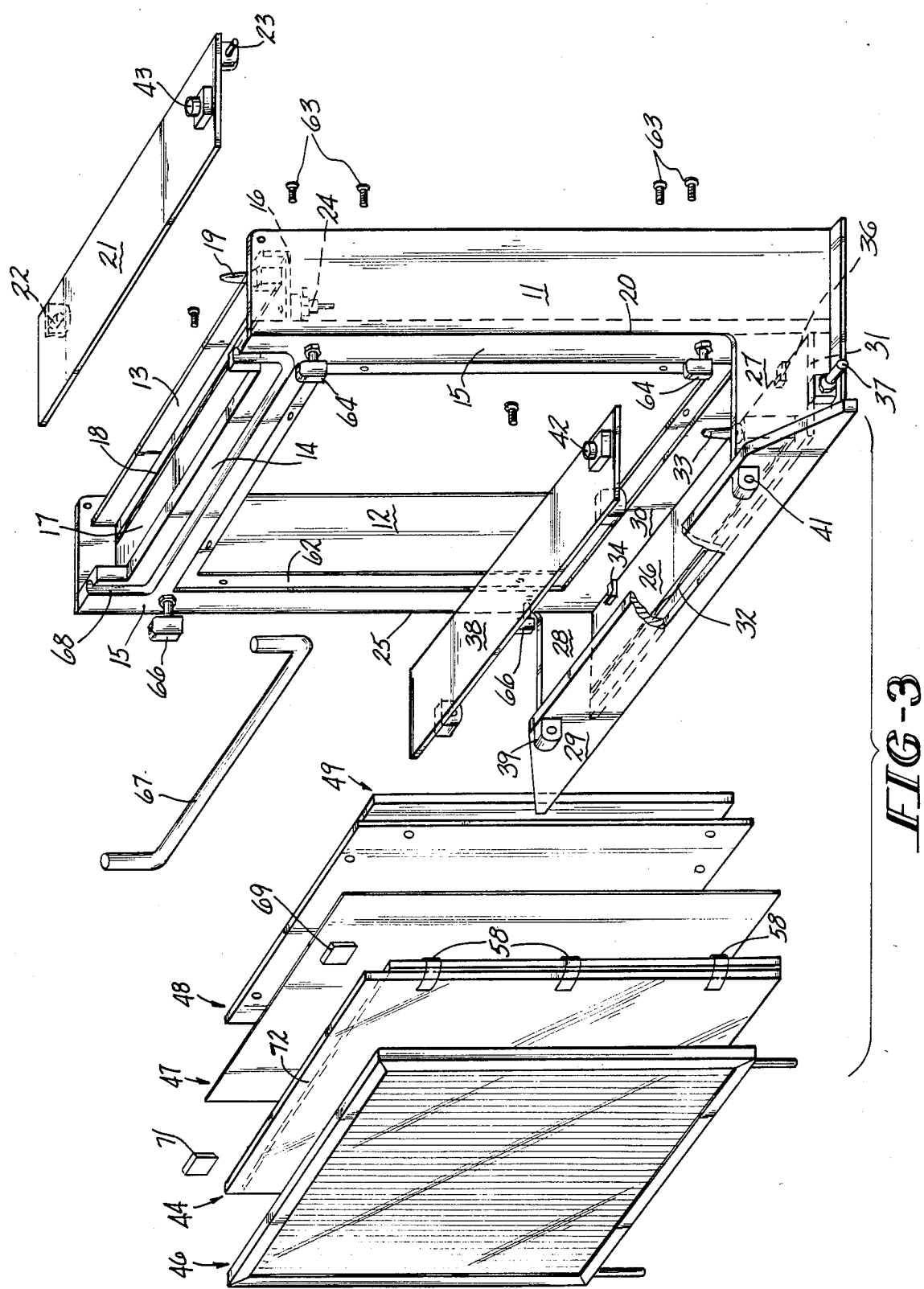
FIG. 3 is an exploded view of the illustration of FIG. 1.

Referring in detail to the drawings, particularly FIGS. 1, 2 and 3, the reference numeral 10 indicates generally a nucleic acid sequencing electrophoresis unit having side supports 11 and 12, main front panel 15 joining side supports at 20 and 25. Rear panel 13, a portion 14 of main front panel 15 and bottom panel 16 define an upper buffer reservoir 17.

The bottom panel 16 is formed with an elongated V-shaped groove to receive a platinum electrode 18 terminating at electrical connector 19.

The reservoir 17 is closed by a top panel 21 hinged to the side supports 11 and 12 by hinge pins 22 and 23. Bottom panel 16 is fitted with a quick operating petcock 24 for convenience in draining and cleaning reservoir 17. A low buffer reservoir 26 is formed by extensions 27 and 28 of side supports 11 and 12 respectively, trapezoidal front panel 29, a portion 30 of main front panel 15 and bottom panel 31.

Here again, the reservoir is formed with a groove to receive a second electrode 32 terminating in an electrical connector 33.

Brackets 34 and 36 are provided for supporting gel mold plates in a manner which will be described as this specification proceeds.

The bottom panel also includes a second petcock 37 facilitating draining and cleansing as called for in the upper reservoir 17.

A closure panel 38 hinged to the front panel 29 at 39 and 41 is formed with an opening 42 to provide clearance for the connector 33.

Correspondingly, the top reservoir closure panel 21 is provided with an opening 43 for receiving the mating electrical connector 19.

Referring in detail to FIG. 3, the various vertical plates and panels are identified as follows:

The reference numeral 44 indicates a gel mold, the numeral 46 indicates a clear lightweight insulating sheet of polycarbonate or the like, the reference numeral 47 denotes a thin thermally conductive silicone rubber sheet or like plastic membrane which also acts as an electrical insulator, the reference numeral 48 designates a sheet of conductive metal such as aluminum or copper for equalizing heat throughout the gel wedge, and finally the reference numeral 49 denotes a cover sheet of plastic, glass or other suitable material for purposes of exterior ornamentation.

Figure 4A:
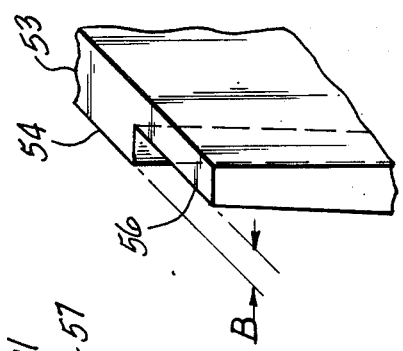
FIGS. 4A and 4B are enlargements of portions of FIG. 4 further detailing how the secondary surface is offset and inclined.
Figure 4B:
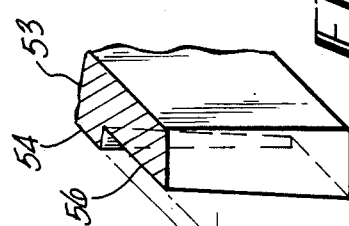
Figure 4:
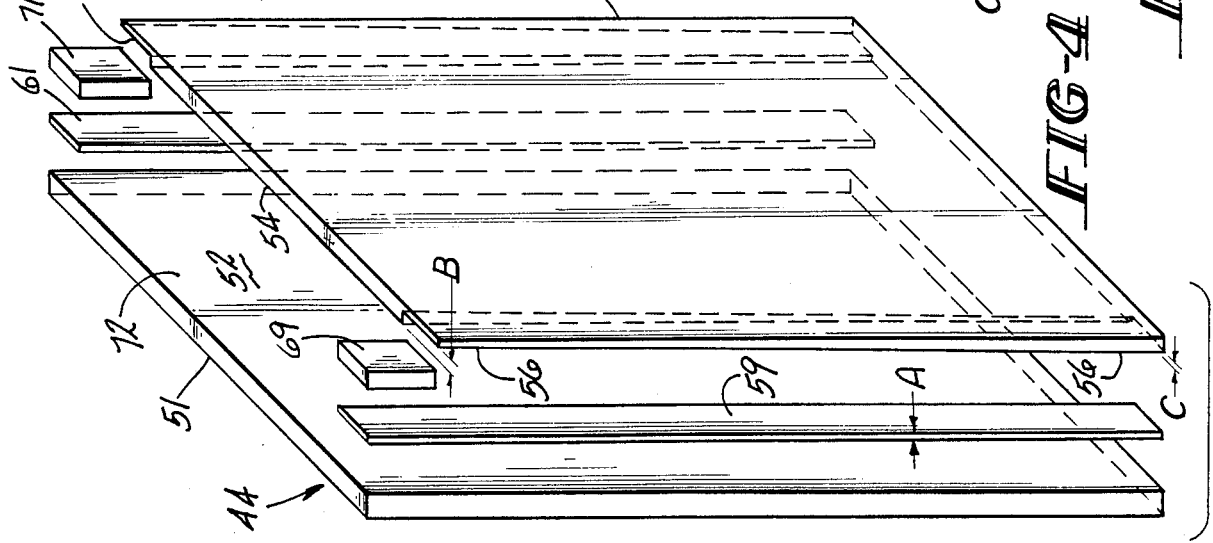
FIG. 4 is an exploded view of the mold plate sandwich of FIG. 2 showing the inclined secondary surfaces of one mold plate.

Referring in detail to FIGS. 4, 4A and 4B the manner of preparing and fabricating the gel mold will be described.

The gel mold 44 comprises a first glass mold plate 51 having a first flat surface 52, a second glass mold plate 53 having a first flat surface 54. Spaced margins of plate 53 are formed, usually by grinding, with inclined second surfaces 56 and 57 where all portions of the second surfaces are offset from the intervening first surface 54.

Note that the mold plates are disposed vertically and the second surfaces 56 and 57 are offset to a greater degree at the top (see dimension B) and to a lesser degree at the bottom (see dimension C).

The effect of these gradually inclined second surfaces 56 and 57 is that when the mold plates are sandwiched together as shown in FIGS. 2 and 3 the gap between the first or primary surfaces 52 and 54 of the mold plates 51 and 53 is smaller at the top than it is at the bottom.

Incidentally, the reference numerals 58—58 in FIG. 3 denote tape for securing the mold plates together temporarily until fixed in the apparatus in a manner which will become apparent as this specification proceeds.

Spacers or gaskets 59 and 61 are fabricated of teflon or of equivalent material and are of uniform thickness A of the order of 1.0 millimeter and approximately one-half inch wide. It is important that the gasket material be inert and exhibit no reaction with a gel or with particles within the gel.

The dimension B at the top of the glass mold plate 53 (only one secondary surface 56 is shown in detail) is of the order of 0.8 millimeters to 1.0 millimeters graduating uniformly to a dimension C at the bottom of the plate of the order of 0.20 to 0.40 millimeters.

The width of the secondary surfaces 56 and 57 are formed to accommodate the width of the spacer or gasket 59 and 61.

Thus, when the mold plates are clamped together under a pressure of the order of 8 psi, the mold cavity is formed defining an inverted wedge or an inverted V-shape in cross-section.

A typical gel mold set-up to create a mold having a gap of 0.3 mm at the top and a gap of 0.9 mm at the bottom using a 1.0 mm rigid teflon spacer is as follows:

A pair of spaced, offset inclines (secondary surfaces) are ground upon glass mold plate 53 so that dimension B (depth of offset at top of inclined secondary surface) equals 0.7 mm and dimension C (depth of offset at bottom of inclined secondary surface) equals 0.1 mm.

Thus, when mold plates 51 and 53 are sandwiched together with a spacer disposed in both offset secondary surfaces a gel mold is created having a truncated, inverted wedge shape in cross-section where the gap at the top is 0.3 mm and the gap at the bottom is 0.9 mm.

The apparatus is assembled by receiving the metal sheet 48 (in this case aluminum) in a peripheral recess 62 formed in front panel 15 and securing the metal sheet to the panel 15 by screws 63—63 (in this case plastic screws).

Decorative or ornamental sheet 49 is secured, usually by adhesive, to the back side of the metal sheet 48. Next silicone rubber sheet 47 is secured adhesively to front side of the metal sheet 48 so that the silicone sheet extends throughout the joint between the recess 62 and the peripheral margin of the metal sheet 48 and overlaps a portion of the main front panel 15.

The mold plates temporarily taped as shown in FIG. 3 are positioned as a unit upon brackets 34 and 36 and spring loaded clamps 64-66 are rotated into clamping position securing the plates together and clamping the plates tightly to main front panel 15.

Note that inner glass mold plate 53 is shorter than mating plate 51 and makes a fluid-tight seal against a U-shaped sealing gasket 67 received in a mating groove 68 formed in front panel 15.

This seal is completed by sealing pads 69 and 71 sandwiched between the front panel 15 and the upwardly projecting portion 72 of first mold plate 51.

This seal is necessary to insure that buffer solution in upper reservoir 17 will overflow its front panel portion 14 into the gel within the gel mold without leaking to other areas.

At this point, the gel mold, temporarily taped, is set upon brackets 34 and 36 and is secured tightly to the front panel 15 by manipulating spring loaded clamps 64-66. That is, the clamps are withdrawn against a spring load (i.e., compressing the spring), rotated and released to apply proper clamping pressure to the mold plates—at least 8 psi.

Note that brackets 34 and 36 are within the lower reservoir 26 so that when buffer solution is introduced the bottom of the gel slab is immersed in buffer solution.

If insulating sheet 46 is required, it is dropped in place forward of the mold and is positioned by guide pins 73—73.

As stated previously, the spring loaded clamps 64-66 have two clamping positions. Thus, these clamps are reset in their second position and are useful to clamp the insulating sheet 46 and the gel mold plates 51 and 53 snugly to the front panel 15 maintaining proper mold clamping pressure.

Buffer reservoir closure panels 21 and 38 are set in place and upon introducing the gel material and appropriate buffer fluid in the upper and lower reservoirs, the unit is ready for operation.

This invention may be embodied in other forms or carried out in other ways without departing from the spirit or essential characteristics thereof. The present embodiment is therefore to be considered as in all respects illustrative and not restrictive, the scope of the invention being indicated by the appended claims, and all changes which come within the meaning and range of equivalency are intended to be embraced therein.

What is claimed is:

1. A mold apparatus for shaping an electrophoresis gel into a wedge-like configuration comprising a pair of plates each having a first flat surface, said plates being spaced apart by a ribbon of gasket material of uniform thickness, spaced margins of one of said plates being offset from said flat surface to define second surfaces, said second surfaces being inclined relative to said first surface and means for clamping the plates together with the gasket material sandwiched between said surfaces.

2. The mold of claim 1 in which the gasket material is dimensioned so as to be substantially coextensive with said second surface.

3. The mold of claim 1 in which the plates are positioned vertically and the second surface is disposed relative to the first surface so that the first surfaces of the respective plates are spaced apart further at the bottom of the plates than at the top thereof when the plates are clamped together.

4. The mold of claim 3 in which the flat first surfaces of the plates define a wedge-shape configuration in cross-section when in the clamped condition and the spacing of the first surfaces throughout said wedge shape is no greater than the thickness of said gasket material.

5. The mold of claim 4 in which the wedge thickness measures in the range of 0.2 mm to 0.4 mm at one end and in the range of 0.8 mm to 1.0 mm at an opposite end.

6. The mold of claim 5 in which the uniform thickness of said gasket material is at least 1.0 mm.

7. The mold of claim 1 in which a thermally conductive sheet is disposed generally parallel to said plates and is coextensive therewith.

8. The mold of claim 7 in which said conductive sheet is selected from a group of thermally conductive materials such as copper, aluminum or silver.

9. The mold of claim 7 in which said conductive sheet is disposed on one side of said plates and an insulating sheet is disposed on the opposite side of said plates.

10. The mold of claim 7 in which said thermally conductive sheet is coated with a thermally conductive, electrical insulating skin.

11. The mold of claim 1 in which the plates are fabricated of glass.

12. The mold of claim 1 including a frame for supporting the mold vertically, said frame including two reservoirs, a first reservoir communicating with a first end of said wedge-like gel configuration and a second reservoir communicating with the opposite end of the wedge-like configuration.

13. The mold of claim 12 in which each reservoir is fitted with a valve means for purging each reservoir independently.

14. The mold of claim 12 in which the frame includes a set of clamping lugs settable to a first position to secure the mold to the frame and to a second position for securing the mold and the insulating sheet compositely to the frame.

15. A method of fabricating a wedge shaped electrophoresis gel slab mold comprising the steps of: providing two mold plates each having generally flat primary surfaces, establishing a pair of matching, inclined secondary surfaces on opposed margins of one of said plates, said secondary surfaces being offset from the adjacent primary surface, disposing a ribbon of gasket material of uniform thickness in areal contact with each of said secondary surfaces, and clamping the plates together with the gasket material sandwiched between the plates.

16. The method of claim 15 plus the steps of:
disposing said mold plates vertically and forming said inclined secondary surfaces on said one plate such that the secondary surface is offset from said primary surface at the top of said one plate a greater distance than the offset at the bottom thereof.

17. The method of claim 15 in which the mold plates are glass and the inclined secondary surfaces are formed by grinding.

18. The method of molding a wedge shaped electrophoresis gel slab comprising the steps of fabricating a mold according to claim 15 and introducing a suitable gel compound into the mold.

19. The method of molding a wedge shaped electrophoresis gel slab comprising the steps of fabricating a mold according to claim 16 plus the step of pouring a suitable gel compound into the mold.

* * * * *